United States Patent
Campbell et al.

[11] Patent Number: 6,136,546
[45] Date of Patent: Oct. 24, 2000

[54] METHOD FOR AIDING IN THE DIAGNOSIS OF IN-FRAME DELETION TYPE CONGENITAL MUSCULAR DYSTROPHY

[75] Inventors: Kevin P. Campbell; Valérie Allamand, both of Iowa City, Iowa; Yoshihide Sunada, Kawaguchi, Japan; Volker Straub, Iowa City, Iowa; Mustafa Salih, Riyadh, Saudi Arabia

[73] Assignee: University of Iowa Research Foundation, Iowa City, Iowa

[21] Appl. No.: 09/057,740

[22] Filed: Apr. 9, 1998

[51] Int. Cl.[7] ............................. G01N 33/53; G01N 1/30; G01N 33/567
[52] U.S. Cl. ..................... 435/7.1; 435/7.92; 435/7.94; 435/7.95; 435/40.5; 435/40.52; 436/503
[58] Field of Search ..................................... 435/7.1, 7.94, 435/7.92, 7.95, 40.5, 40.52; 436/503

[56] References Cited

PUBLICATIONS

Leivo L et al PNAS 85:1544–1548, 1988.
Engvall E et al. *J Cell Biol* 103:2457–2465, 1986.
Helbling–Leclerc et al., *Nat. Genet.* 11: 216–218 (1995).
Nissinen et al., *Am. J. Hum. Genet.* 58: 1177–1184 (1996).
Fardeau et al., *Rev. Neurol.* (*Paris*) 152: 11–19 (1996).
Sunada et al., *Hum. Mol. Gent.* 4: 1055–1061 (1995).
Xu et al., *Nat. Genet.* 8: 297–301 (1994).
Zhang et al., *J. Biol Chem.* 271: 27664–27669 (1996).
Allamand et al., *Hum. Mol. Genet.* 6: 747–752 (1997).

*Primary Examiner*—Mark Navarro
*Assistant Examiner*—Li Lee
*Attorney, Agent, or Firm*—Kevin M. Farrell

[57] ABSTRACT

Disclosed are compositions and methods for aiding in the diagnosis of congenital muscular dystrophy associated with in-frame deletion in the laminin-2 α2 polypeptide chain in an individual. In a preferred diagnostic method embodiment, an experimental muscle tissue sample is provided from the individual and treated if necessary to render components available for antibody binding. The components of the sample are then separated on the basis of molecular weight. The separated protein components are then transferred to a solid support while maintaining the relative positions established in separation step. The transferred components are then stained with an affinity reagent which is known to bind to a C-terminal domain of the laminin-2 α2 polypeptide chain. Individual afflicted with congenital muscular dystrophy associated with in-frame deletion in the laminin-2 α2 polypeptide chain on the basis of positive staining in combination with reduced molecular weight of the laminin-2 α2 polypeptide chain relative to the wild-type laminin-2 α2 polypeptide chain. A preferred composition is a nucleic acid probe for the detection of merosin deletion-type congenital muscular dystrophy. The preferred nucleic acid probe is characterized by the ability to bind specifically to a mutant merosin nucleic acid sequence, the mutant merosin nucleic acid sequence comprising a T to C substitution at position 3973 +2 of the consensus donor splice site of exon 25.

10 Claims, 1 Drawing Sheet

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: PCR Primer

<400> SEQUENCE: 1
aggctgagca gaccattcta                                            20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: PCR Primer

<400> SEQUENCE: 2
ccttgttcag ctacctccat                                            20

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: PCR Primer

<400> SEQUENCE: 3
cacaccattt ggagatttat c                                          21

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: PCR Primer

<400> SEQUENCE: 4
tcgggtcaca gttctatgg                                             19
```

METHOD FOR AIDING IN THE DIAGNOSIS OF IN-FRAME DELETION TYPE CONGENITAL MUSCULAR DYSTROPHY

BACKGROUND OF THE INVENTION

Laminins are a family of large extracellular glycoproteins which display a complex and still unclear repertoire of biological functions. Laminin-2, the isoform involved in congenital muscular dystrophy (CMD), is specifically expressed in the basal lamina of striated muscle and peripheral nerve. As are all members of the laminin family, it is composed of three chains: one heavy ($\alpha 2$) and two light chains ($\beta 1$ and $\gamma 1$) that assemble in a cross-shaped molecule with three short arms and one long arm. The C-terminal ends of each chain interact to form the triple stranded long arm of the molecule, stabilized by disulfide bonds, with a large globular (G) domain contributed to by the $\alpha 2$-chain. The $\alpha 2$-chain of laminin consists of 6 domains: I and II are part of the long arm; IIIa, IIIb and V contain cystein-rich EGF-like repeats and are predicted to have rigid rod-like structures; and IVa, IVb and VI are predicted to form globular structures. Laminin $\alpha 2$-chain has been shown to be a native ligand for $\alpha$-dystroglycan, an extracellular component of the dystrophin-associated glycoprotein complex (DGC). This complex constitutes a link between the subsarcolemmal skeleton and the extracellular matrix. A number of components of the DGC have now been shown to be involved in muscular dystrophies suggesting a crucial role of laminin-2 and the components of the DGC in maintaining the integrity of muscle cell function.

Congenital muscular dystrophy (CMD) is a clinically and genetically heterogeneous group of autosomal recessive neuromuscular disorders of early onset. In the classic form of CMD, clinical manifestations are limited to skeletal muscle with no clinical involvement of the central nervous system (CNS) although changes in the white matter have been detected by MRI. The histological changes in muscle biopsies consist of connective tissue proliferation, large variation in the size of the muscle fibers as well as some necrotic and regenerating fibers.

Two groups of classical-type CMD cases can be distinguished according to the status of the $\alpha 2$-chain of laminin-2 (also referred to as merosin) with about half of the cases displaying a deficiency of this protein. However, even these merosin-deficient CMD cases represent a heterogeneous subgroup since some patients display a total deficiency of the $\alpha 2$-chain of laminin-2 whereas this protein is expressed in others, though at a reduced level. Linkage analyses and homozygosity mapping studies have led to the localization of the CMD locus to chromosome 6q2 (Hillaire et al., *Hum. Mol. Genet.* 3: 1657–1661 (1994); and Helbling-Leclerc et al., *C. R. Acad. Sci. Paris* 318: 1245–1252 (1995)), in the region containing the gene encoding the $\alpha 2$-chain of laminin (LAMA-2) (Vuolteenaho et al., *J. Cell Biol.* 124: 381–394 (1994)). Recently, mutations affecting this gene have been identified in CMD patients (Helbling-Leclerc et al., *Nat. Genet.* 11: 216–218 (1995); and Nissinen et al., *Am. J. Hum. Genet.* 58: 1177–1184 (1996)).

The expression of the $\alpha 2$-chain of laminin-2 is also altered in the *dystrophia muscularis* (dy) mouse (Michelson et al., *Proc. Natl. Acad. Sci. USA.* 41: 1079–1084 (1955); Arahata et al., *Proc. Japan Acad.* 699: 259–264 (1993); Sunada et al., *J. Biol. Chem.* 269: 13729–13732 (1994); and Xu et al., *Proc. Natl. Acad. Sci. USA* 91: 5572–5576 (1994)) and its allelic variant ($dy^{2J}$). A splice mutation affecting the murine gene encoding this protein, localized on chromosome 10 (Sunada et al., *J. Biol. Chem.* 269: 13729–13732 (1994)) has recently been identified in the $dy^{2J}$ mouse, resulting in the expression of a truncated protein (Xu et al., *Nat. Genet.* 8: 297–301 (1994); and Sunada et al., *Hum. Mol. Genet.* 4: 1055–1061 (1995)). Interestingly, the $dy^{2J}$ mouse displays a less severe phenotype than the dy mouse which lacks the laminin $\alpha 2$-chain.

Diagnostic and therapeutic developments useful in connection with merosin-deficient CMD cases will require a better understanding of the etiology of the disorder at the molecular level. Such understanding will yield diagnostic kits and ultimately methods for therapeutic intervention.

SUMMARY OF THE INVENTION

The present invention relates to compositions and methods for aiding in the diagnosis of congenital muscular dystrophy associated with in-frame deletion in the laminin-2 $\alpha 2$ polypeptide chain in an individual. In a preferred diagnostic method embodiment, an experimental muscle tissue sample is provided from the individual and treated if necessary to render components available for antibody binding. The components of the sample are then separated on the basis of molecular weight. The separated protein components are then transferred to a solid support while maintaining the relative positions established in separation step. The transferred components are then stained with an affinity reagent which is known to bind to a C-terminal domain of the laminin-2 $\alpha 2$ polypeptide chain. Individual afflicted with congenital muscular dystrophy associated with in-frame deletion in the laminin-2 $\alpha 2$ polypeptide chain on the basis of positive staining in combination with reduced molecular weight of the laminin-2 $\alpha 2$ polypeptide chain relative to the wild-type laminin-2 $\alpha 2$ polypeptide chain.

A preferred composition is a nucleic acid probe for the detection of merosin deletion-type congenital muscular dystrophy. The preferred nucleic acid probe is characterized by the ability to bind specifically to a mutant merosin nucleic acid sequence, the mutant merosin nucleic acid sequence comprising a T to C substitution at position 3973 +2 of the consensus donor splice site of exon 25.

DETAILED DESCRIPTION OF THE INVENTION

Figure 1:
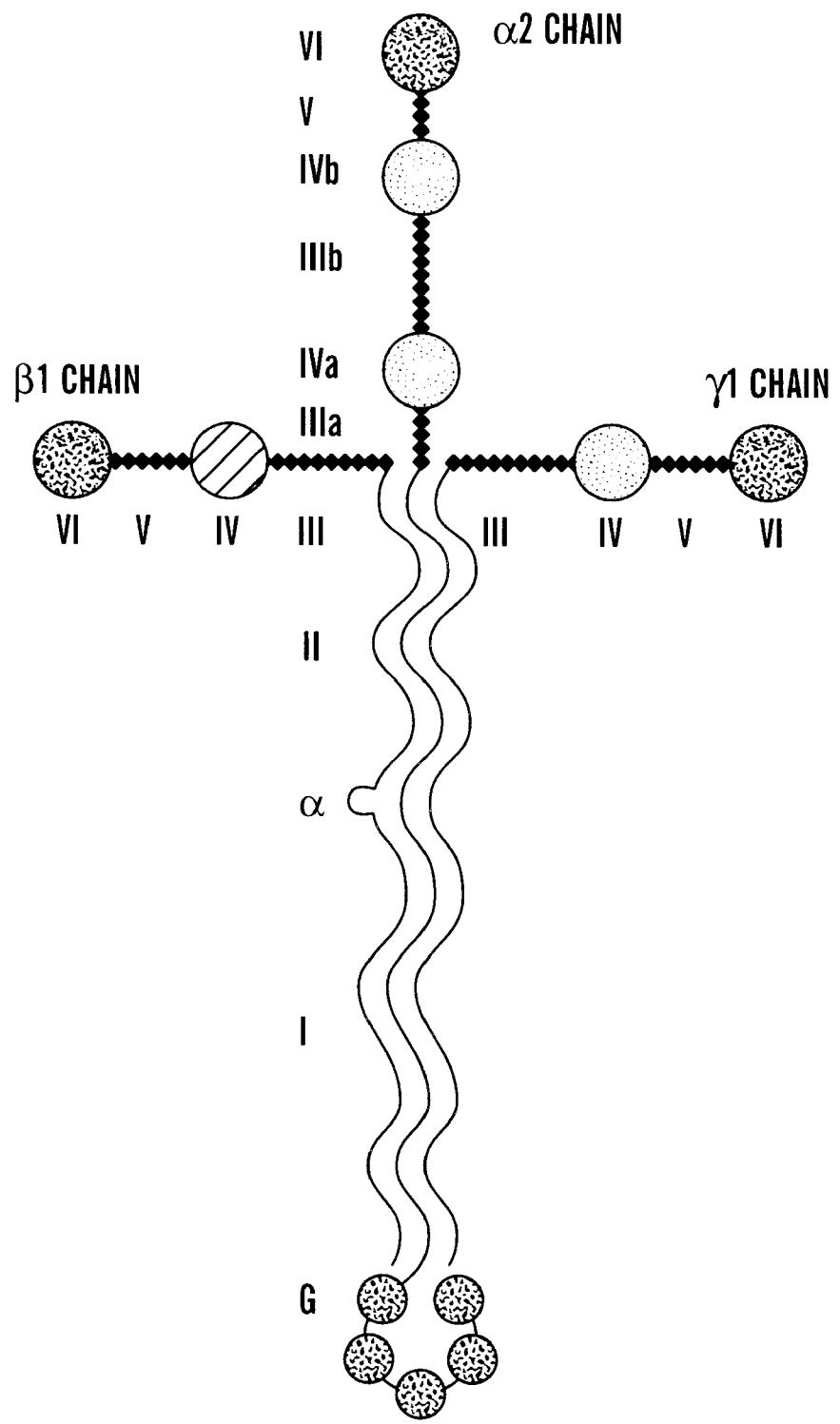
FIG. 1 is a diagrammatic representation of the organization of the laminin-2 trimer.

The present invention is based on the discovery that an in-frame deletion in a laminin-2 subunit is responsible for a previously unknown genus of congenital muscular dystrophy. More specifically, as discussed in greater detail below, molecular analysis was applied to muscle biopsy tissue from individuals diagnosed with CMD. This analysis resulted in the identification of a T→C substitution at position +2 of the consensus donor splice site of exon 25 of the LAMA-2 subunit of laminin-2. This mutation was determined to induce the splicing of exon 25 by alternately using the donor splice site of exon 24. This resulted in the production of a laminin-2 LAMA-2 subunit containing an internal deletion of 63 amino acid residues falling within domain IVa, on the short arm of the protein (FIG. 1). Previous work in mice, discussed briefly above, has identified a similar mutation in domain VI on the short arm of the protein (FIG. 1).

Thus, in one aspect, the present invention relates to a method for aiding in the diagnosis of congenital muscular dystrophy associated with in-frame deletion in the laminin-2 α2 polypeptide chain in an individual. The method is based on the finding that such mutations have been identified on the short arm of the α2 polypeptide chain. Thus, such a pathology can be diagnosed in an individual by analyzing the α2 polypeptide chain to determine whether the C-terminus is intact, followed by an assessment of the molecular weight of the α2 polypeptide chain and comparison of this molecular weight to the known molecular weight of the laminin-2 α2 polypeptide chain from an individual who is not afflicted with congenital muscular dystrophy.

The use of an affinity reagent, such as a monoclonal or polyclonal antibody preparation, may be used to determine whether the C-terminus of the α2 polypeptide is intact. The production of appropriate antibodies and the development of appropriate assays is a matter of routine experimentation. Referring to FIG. 1, for example, the C-terminus of the α2 polypeptide can be seen to comprise domains G, I and II. Techniques for the isolation of the α2 polypeptide are known, as is the nucleic acid sequence which encodes it. Thus, appropriate epitope-containing C-terminal domains may be isolated, or produced by recombinant DNA techniques, and used to immunize an animal. Monoclonal and polyclonal antibodies are generated by conventional techniques and used in a binding assay to determine C-terminal epitope integrity.

For example, one type of binding assay is referred to in the art as a Western blot. In this technique, muscle tissue is isolated, solubilized and the polypeptide components are separated by denaturing gel electrophoresis in at least one dimension. The separated components are then transferred to a solid matrix, and the transferred components are then stained using an affinity reagent (e.g., an antibody) specific for a C-terminal epitope of the α2 polypeptide. Positive staining is an indication of C-terminal integrity. As an alternative to the Western blot technique, muscle tissue cryosections may be prepared and stained with the preferred affinity reagent. In all cases, otherwise identical affinity reagent staining should be conducted using samples from an individual who is not afflicted with congenital muscular dystrophy. This individual would serve as the negative control in such diagnostic procedures.

Positive staining using the affinity reagent specific for the C-terminus of the α2 polypeptide is one element of the diagnostic method. Following confirmation of C-terminal integrity, it is necessary to determine the molecular weight of the α2 polypeptide from the individual, and compare this determined molecular weight to the molecular weight of the α polypeptide from an individual who is not afflicted with congenital muscular dystrophy. A straight-forward method for determining the relative molecular weights is by denaturing gel electrophoresis. Reduced molecular weight of the α2 polypeptide chain, in combination with a determination of an intact C-terminal region, is diagnostic of congenital muscular dystrophy associated with in-frame deletion in the laminin-2 α2 polypeptide chain in the individual.

In another aspect, the present invention relates to a nucleic acid probe for the detection of congenital muscular dystrophy associated with in-frame deletion in the laminin-2 α2 polypeptide chain. In one embodiment, the nucleic acid probe is characterized by the ability to bind specifically to a mutant merosin nucleic acid sequence, the mutant merosin nucleic acid sequence comprising a T to C substitution at position 3973 +2 of the consensus donor splice site of exon 25.

EXEMPLIFICATION i) Materials and Methods

Patients

A 3½ year old boy (Case 1), was referred to King Khalid University Hospital because of muscle weakness and delay in motor development. He showed muscle hypotonia and could not control his head when pulled to a sitting position after the age of 5 months. Although he could roll over at 5 months and sit independently at 7 months, he never attempted crawling but was ultimately able to walk at 26 months of age. Thereafter, he stumbled easily and had difficulty raising from the sitting position. His 2½ year old sister (Case 2) also showed hypotonia since early infancy and had poor head control. She eventually achieved walking at the age of 3 years and 8 months. Both pregnancies had been carried to term and both deliveries had been normal. Both patients are still walking at the present time. In both cases, investigations revealed normal electrocardiogram and nerve conduction but electromyography showed myopathic features. Serum creatine kinase levels of Case 1 were elevated (1187 U/L, Control <180 U/L) whereas they were only slightly raised in Case 2 (256 U/L).

Immunohistochemistry

Seven μm-thick skeletal muscle cryosections were prepared from normal control tissue and CMD Cases 1 and 2 biopsy specimens. Indirect immunofluorescence microscopy was performed as previously described (Sewry et al., *Lancet* 347: 582–584 (1996)). Monoclonal anti-human laminin α2-chain antibody, clone 5H2, recognizing the G-domain of the protein (Leivo et al., *Proc. Natl. Acad. Sci. USA* 87, 3264–3268 (1990), Earwicker et al., *Cell Regul.* 1, 731–740 (1990)) was purchased from GIBCO-BRL. A protein containing the last 1444 residues of the human laminin α2-chain was generated by transfecting insect Sf9 cells with the corresponding α2-chain cDNA fragment cloned into pVL1392ss, a modified baculovirus expression vector. The secreted α2(G) protein was purified to homogeneity as described previously (Yurchenco, et al., *J. Biol. Chem.* 268, 8356–8365 (1993)). Rabbit polyclonal antibodies were generated through successive rounds of immunization using 0.2 mg of protein in complete Freund's Adjuvent. Total IgG fraction was obtained using protein A affinity chromatography. Monoclonal antibody 4H8-2 was raised in rat to native mouse laminin-2 (Schuler and Sorokin, *J. Cell Sci.* 108, 3795–3805 (1995)). Specificity for laminin α2-chain was demonstrated by reaction with laminin-2, but not laminin-1 in ELISA, immunoprecipitation and Western blots. Cross-reaction with human laminin α2-chain was described in (Ohlendieck et al., *Neurology* 43, 795–800 (1993)). The sections were examined under a Zeiss Axioplan fluorescence microscope. Photographs were taken under identical conditions with the same exposure time.

Immunoblotting

Biopsied skeletal muscle cryosections from normal control and CMD Cases 1 and 2 were subjected to the procedure previously described (Sunada et al., *Hum. Mol. Genet.* 4: 1055–1061 (1995)) except that the detection was performed using the enhanced chemiluminescence system (ECL kit RPN 2101; Amersham). Rabbit polyclonal anti-laminin α2-chain antibodies were generated as previously described (Lim et al., *Nat. Genet.* 11, 257–265 (1995)) against a murine GST-fusion protein spanning amino acid residues 1682 to 1884, which are located within domains I+II of the long arm of the laminin α2-chain.

RT-PCR

Total RNA was prepared from biopsy samples using RNAzol (Tel-Test, Friendswood, Tex.) according to the manufacturer's directions. Single-stranded cDNA was generated by reverse transcription with Stratascript (Stratagene) using an oligo-(dT)$_{18}$ primer. Several primer couples spanning the entire cDNA previously described (Hayashi et al., *Muscle and Nerve* 18, 1027–1030 (1995)) or designed specifically for these studies (Forward primer 5'-AGGCTGAGCAGACCATTCTA-3' SEQ ID NO: 1, Reverse primer 5'-CCTTGTTCAGCTACCTCCAT-3' SEQ ID NO: 2 at positions 3615 and 4124 of the cDNA sequence, respectively) were used for amplification. One tenth of the single-stranded cDNA was subjected to PCR amplification in a final volume of 50 µl containing 10 mM Tris-HCl, 1.5 mM MgCl$_2$, 50 mM KCl pH8.3 and 100 ng of each primer. After 5 min at 94° C., 200 µM of each dNTP and 2.5 Units of Taq polymerase (Boehringer Mannheim) were added, and 35 cycles were carried out as follows: 40 sec denaturation at 94° C., 30 sec annealing at the appropriate temperature and 30 sec extension at 72° C. Five µl of PCR products were analyzed by electrophoresis on 2% Seakem agarose gel stained with ethidium bromide.

Genomic DNA amplification

Fifty to one hundred ng of genomic DNA from each member of the family were used as a template for PCR amplification. Reactions were performed as described above. To amplify the region surrounding the deletion, a forward primer designed in an intronic sequence (5'-CACACCATTTGGAGATTTATC-3' SEQ ID NO: 3) was used in combination with a reverse primer designed in an exonic sequence (5'-TCGGGTCACAGTTCTATGG-3' SEQ ID NO: 4). Thirty five cycles of amplifications were performed as described above with an annealing temperature of 55° C. Five µl of PCR products were analyzed by electrophoresis on 2% Seakem agarose gel stained with ethidium bromide.

Sequencinq

Prior to sequencing, PCR products were purified using the QIAquick PCR purification kit (QIAGEN). DNA sequencing was performed using the dye terminator cycle sequencing chemistry with AmpliTaq™ DNA polymerase, FS enzyme, and was analyzed on a 373A Stretch Fluorescent Automated Sequencer (Applied Biosystem).

ii) Results

Muscle biopsies from the vastus lateralis taken from two siblings from a consanguineous Saudi Arabian family diagnosed with CMD showed replacement of muscle fibers by fat tissue associated with an increase in endomysial and perimysial connective tissue. There was a wide variation in fiber size. Both atrophic and markedly hypertrophic fibers were observed along with a few hyalin fibers. In addition, there were degenerating, regenerating and split fibers. Immunofluorescence analysis of skeletal muscle sections using a monoclonal (Leivo et al., *Proc. Natl. Acad. Sci. USA* 87, 3264–3268 (1990), Earwicker et al., *Cell Regul.* 1, 731–740 (1990)) or a polyclonal antibody (see details in Materials and Methods) recognizing the G-domain of the laminin α2-chain revealed a near normal level of expression of the protein in both CMD patients compared to normal control tissue. However, a drastic reduction of the staining was seen with a monoclonal antibody raised against the N-terminal region of the protein (Schuler and Sorokin, *J. Cell Sci.* 108, 3795–3805 (1995)).

Immunoblotting analysis suggested the expression of a truncated protein in these patients since two bands of approximately 170 kDa and 120 kDa were identified using a polyclonal anti-α2-chain antibody which detected a N-terminal fragment of 300 kDa in normal control skeletal muscle. These bands likely represented proteolytic fragments of the protein. However, the truncated α2-chain still seemed capable of assembly with chains β1 and γ1 since the heterotrimeric molecule was detected. Correspondingly, in vitro studies showed that the deletion identified in the dy$^{2J}$ mouse seem to render the protein more sensitive to proteolysis.

In both patients, magnetic resonance imaging of the brain showed no evidence of atrophy but increased signal intensities in the white matter on T2-weighted images, as typically seen in this disease. The spread of the white matter changes appeared wider in Case 2, with a distribution pattern more pronounced around occipital horns of the lateral ventricles, but also anteriorly around the temporal horns and at the level of the centrum semiovale.

Because of the consanguinity existing in this family, it was assumed that both affected siblings were likely to be homozygous for the same mutation. Therefore, experiments were arbitrarily focused on Case 1. RT-PCR amplification was performed using a variety of oligonucleotide primers scattered along the cDNA sequence of the LAMA2 gene and obtained a smaller fragment in Case 1 for one set of primers. Direct sequencing of this PCR product revealed a 189 bp in-frame deletion resulting in the deletion of 63 amino acid which falls into domain IVa, on the short arm of the protein. Based on the genomic structure of the LAMA2 gene (Zhang et al., *J. Biol. Chem.* 271, 27664–27669 (1996)), primers surrounding the deletion were designed and used for amplification on DNA of all members of the family. Direct sequencing of the PCR products allowed the identification of a T→C substitution at position +2 of the consensus donor splice site of exon 25. This mutation was found in a homozygous state in both patients and induced the splicing of exon 25 by alternately using the donor splice site of exon 24. As expected, both parents were heterozygotes. The unaffected son of this family did not carry the mutation. This mutation was not found on 94 chromosomes from non-related individuals.

Thus, disclosed herein is a novel mutation in the human gene encoding the laminin α2-chain which leads to the expression of an internally deleted protein. The results obtained by immunofluorescence analysis with antibodies recognizing different domains of the laminin α2-chain revealed that both antibodies recognizing the G-domain of the protein detected a near normal level of expression of the protein with only a few fibers showing a patchy pattern. On the contrary, the use of antibodies recognizing the N-terminal region of the protein revealed a substantial reduction in the expression of the protein, consistent with the deletion in domain IVa of the protein. These results demonstrate that using more than one antibody can provide valuable indications as to which domain(s) of the laminin α2-chain may be affected in CMD patients.

The mutation identified here is similar to that found in the dy$^{2J}$ mouse (Xu et al., *Nat. Genet.* 8: 297–301 (1994), Sunada et al., *Hum. Mol. Genet.* 4: 1055–1061 (1995)), i.e. a nucleotide change in a donor splice site leading to an aberrant splicing mechanism and to the expression of a truncated laminin α2-chain. In both cases presented here, as well as in the dy$^{2J}$ mouse, the in-frame deletion occurred in the short arm of the laminin α2-chain, known to be involved in the formation of a laminin network in basement membranes (Yurchenco et al., *J. Cell. Biol.* 117, 1119–1133 (1992), Yurchenko and Cheng, *J. Biol. Chem.* 268, 17286–17299 (1993)). While not wishing to be bound by theory, it appears that in the dy$^{2J}$ mouse as well as in these patients that the deletion disrupts the formation of the laminin network rendering the protein more sensitive to proteolysis as suggested by the immunoblotting analysis. The protein may therefore not be able to assume its role of link between the extracellular matrix and the dystrophin-glycoprotein complex via dystroglycan.

At the clinical level, it is worth noting that the two CMD cases presented here appear to be less severely affected than the merosin-deficient cases described in the literature (Fardeau et al., *Rev. Neurol.* (*Paris*) 152, 11–19 (1996)). Correspondingly, the phenotype of the dy$^{2J}$ mouse is milder than that of the dy mouse which presents a drastic reduction in the expression the protein (Xu et al., *Nat. Genet.* 8: 297–301 (1994)). This situation is reminiscent of the Duchenne and Becker muscular dystrophy cases: while Duchenne patients are very severely affected and often display out of frame deletions in the dystrophin gene, the mildly affected Becker patients have in-frame deletions in this gene.

a) providing an experimental muscle tissue sample from the individual, treated if necessary to render components available for antibody binding;
b) separating the components of the sample on the basis of molecular weight;
c) transferring protein components separated in step b) to a solid support while maintaining the relative positions established in separation step b);
d) staining the protein components attached to the solid support of step c) with an affinity reagent which is known to bind to a C-terminal domain of the laminin-2 α2 polypeptide chain; and
e) identifying an individual afflicted with congenital muscular dystrophy associated with in-frame deletion in the laminin-2 α2 polypeptide chain on the basis of:
  i) positive staining in step d); and

What is claimed is:

1. A method for aiding in the diagnosis of congenital muscular dystrophy associated with in-frame deletion in the laminin-2 α2 polypeptide chain in an individual human, comprising the steps of:

ii) reduced molecular weight of the laminin-2 α2 polypeptide chain relative to the wild-type laminin-2 α2 polypeptide chain.

2. The method of claim 1 wherein the affinity reagent is an antibody.

3. The method of claim 2 wherein the antibody is a monoclonal antibody.

4. The method of claim 2 wherein the antibody is a polyclonal antibody.

5. The method of claim 1 wherein the C-terminal domain of the laminin-2 α2 polypeptide chain is selected from the group consisting of domains G and I+II.

6. A method for aiding in the diagnosis of congenital muscular dystrophy associated with in-frame deletion in the laminin-2 α2 polypeptide chain in an individual human, comprising the steps of:

a) analyzing the laminin-2 α2 polypeptide chain to verify the C-terminus is intact by:
      i) providing muscle tissue cryosection from the individual; and
      ii) staining the muscle tissue cryosection with an affinity reagent which is known to bind to a C-terminal domain of the laminin-2 α2 polypeptide chain;
   b) assessing the molecular weight of the patient's laminin-2 α2 polypeptide chain by:
      i) providing an experimental muscle tissue sample from the individual, treated if necessary to render components available for antibody binding;
      ii) separating the components of the sample on the basis of molecular weight and comparing the molecular weight of the laminin-2 α2 polypeptide chain from the muscle tissue of the individual to the molecular weight of wild-type laminin-2 α2 polypeptide chain; and
   c) identifying an individual afflicted with congenital muscular dystrophy associated with in-frame deletion in the laminin-2 α2 polypeptide chain on the basis of:
      i) confirmation of an intact C-terminus of laminin-2 α2 polypeptide by positive staining in step a)ii); and
      ii) reduced molecular weight of the laminin-2 α2 polypeptide chain relative to the wild-type laminin-2 α2 polypeptide chain.

7. The method of claim 6 wherein the affinity reagent is an antibody.

8. The method of claim 7 wherein the antibody is a monoclonal antibody.

9. The method of claim 7 wherein the antibody is a polyclonal antibody.

10. The method of claim 6 wherein the C-terminal domain of the laminin-2 α2 polypeptide chain is selected from the group consisting of domains G, I and II.

* * * * *